United States Patent [19]
Kaplan et al.

[11] Patent Number: 5,722,428
[45] Date of Patent: Mar. 3, 1998

[54] METHOD FOR PRODUCING A POSTERIOR VITREOUS DETACHMENT

[75] Inventors: Henry J. Kaplan; Tongalp H. Tezel, both of St. Louis, Mo.

[73] Assignee: Washington University, St. Louis, Mo.

[21] Appl. No.: 740,430

[22] Filed: Oct. 29, 1996

[51] Int. Cl.⁶ .................................................. A61B 19/00
[52] U.S. Cl. .................................... 128/898; 604/51
[58] Field of Search ................................. 128/898, 899; 604/51, 289–290, 294

[56] References Cited

U.S. PATENT DOCUMENTS 5,292,509  3/1994  Hageman.
5,304,118  4/1994  Trese et al. ............................ 604/51 X

OTHER PUBLICATIONS

Webster's II New Riverside University Dictionary, 1994, (pp. 356, 1116).
O'Neill & Shea, Canad. J. Ophthalmol. 8:366–370, 1973.
Moorehead, et al., Arch. Ophthalmol. 98:1829–1839, 1980.
Verstraeten et al., Arch. Ophthalmol. 111:849–854, 1993.
Tezel, et al., ARVO Abstract, 1996.
Hesse, et al., Invest. Ophthalmol. Vis. Sci. vol. 36, ARVO Abstract No. 3492-479, 1995.

*Primary Examiner*—John P. Lacyk
*Assistant Examiner*—Ryan Carter
*Attorney, Agent, or Firm*—Wolf, Greenfield & Sacks, P.C.

[57] ABSTRACT

Methods for enzymatic production of a posterior vitreous detachment are provided. In preferred methods, dispase is used to cleave type IV collagen and fibronectin at the vitreoretinal junction to promote the posterior vitreous detachment. The methods provide for enzymatic treatment in conjunction with intraocular surgery as well as treatments to relieve the blinding complications of certain eye disorders without the need for surgery. Also disclosed are kits for production of a posterior vitreous detachment and devices containing the enzymes useful in the methods.

17 Claims, No Drawings

METHOD FOR PRODUCING A POSTERIOR VITREOUS DETACHMENT

GOVERNMENT SUPPORT

This work was funded in part by the National Institutes of Health under the Grant No. EY-02687. The Government may retain certain rights in this invention.

BACKGROUND OF THE INVENTION

The vitreous is a clear, proteinaceous mass which fills the posterior cavity of the eye between the lens and the retina. The vitreous is attached at its posterior face to the retina along the structure known as the internal limiting membrane. This site of attachment of the vitreous and the retina is termed the vitreoretinal junction and consists of a layer of basement membrane proximal to the retina and a layer of collagen fibrils proximal to the vitreous.

Degenerative changes in the vitreous are a precursor to posterior vitreous detachment. Degeneration of the vitreous is part of the normal aging process, but also may be induced by pathological conditions such as diabetes, Eales' disease and uveitis (Gloor, B. P., "The Vitreous", in *Adler's Physiology of the Eye*, C. V. Mosby, St. Louis, Mo., 1987). Because the vitreous is attached to the retina, the receding vitreous can precipitate a retinal tear, with subsequent detachment of the retina.

Certain pathological conditions of the eye are accompanied by the formation of new (abnormal) vessels on the surface of the retina—namely proliferative diseases. With a posterior vitreous detachment traction is placed on new vessels causing rupture and bleeding. Proliferative retinal diseases thus are accompanied by both a high probability of retinal detachment as well as complications from bleeding resulting from the rupture of the newly formed blood vessels.

There are no current effective pharmacologic techniques to product a posterior vitreous detachment before the development of proliferative disease, e.g. in diabetes, or to allow surgery on or beneath the retina. Therefore, vitreous detachment can only be achieved mechanically—i.e. by surgery. Although effective, such surgeries require a high level of skill in the practitioner to avoid permanent damage to the retina, and are frequently accompanied by retinal tears and/or retinal detachment.

Accordingly, it has been a goal of ophthalmologists to develop an alternative to surgical detachment of the vitreous. Knowledge of the molecular components of the vitreous, the vitreoretinal junction and the internal limiting membrane provided guideposts for the development of prior art non-surgical methods of posterior vitreous detachment.

For example, U.S. Pat. No. 5,292,509 describes a method of detaching the vitreous body by injection of a protease-free glycosaminoglycanase, preferably chondroitinase ABC, into the vitreous cavity to degrade chondroitin sultafe glycosaminoglycan/proteoglycan.

Other investigators have concentrated on the collagen component of the vitreous on the hypothesis that collagen fibrils attach the vitreous to the retina. O'Neill and Shea (Canad. J. Ophtal. 8:366, 1973) described the use of bacterial collagenase (1.2 µg–1.0 mg) injected directly into the vitreous and observed the effects on the fibrillar structure of the vitreous after 6 to 17 days. The collagenase injection resulted in disruption of the fibrillar structure in the vitreous, and the internal limiting membrane, as well as disruption of the outer layers of the retina. To minimize the side effects of vitreous liquefaction and retinal damage, the authors suggested using larger doses of the bacterial collagenase enzyme, up to 5 mg, for 24 to 72 hours.

More recently, Moorehead, et al. (Arch. Opthalmol. 98:1829–1839, 1980) evaluated the use of a bacterial collagenase (clostridiopeptidase A) to digest cicatricial scar tissue without damaging the retina and the internal limiting membrane. The specific collagerinse used was chosen because it effectively digests the interstitial (blood vessel wall) collagen which composes the scar tissue without digesting basement membrane collagen which is present in the retina and internal limiting membrane. Following a 30 minute exposure of rabbit eyes to the collagenase clostridiopeptidase A, the authors reported the blood vessel collagen was destroyed without any effect on the basement membrane collagen of the retina and internal limiting membrane or the fine fibrils of vitreal collagen at the retina. The authors also noted that it was essential that the intravitreal use of collagerinse be followed by conventional vitrectomy (surgical extraction of the contents of the vitreous cavity) to remove the collagerinse from the eye. Failure to remove the collagenase was reported to lead to degradation of the internal limiting membrane and the posterior lens capsule as well as hemorrhage from optic disk blood vessels.

The unsatisfactory qualities of collagerinse treatments, described above, has prompted searches for other enzymes to induce posterior vitreous detachment. Verstraeten et al. (Arch. Ophthalmol. 11:849–854, 1993) proposed the use of plasmin, a serine protease, to produce a cleavage at the vitroretinal interface. Plasmin hydrolyzes glycoproteins, including laminin and fibronectin, which are found at the vitreoretinal junction. Plasmin treatment was performed with or without subsequent vitrectomy. The authors noted that eyes treated with plasmin showed some areas of posterior vitreous detachment, but only after vitrectomy was the vitreous substantially detached. The authors concluded that plasmin treatment may be useful as a biochemical adjunct to mechanical vitrectomy.

A satisfactory non-surgical method for producing a posterior vitreous detachment has not yet been discovered, but is needed because of the deficiencies of the prior art methods described above. In particular, a method that does not require surgery for complete posterior vitreous detachment is needed to avoid the complications Of mechanical separation of the vitreous and the retina with its accompanying potential of retinal tear or retinal detachment. Preferably the method does not produce a posterior vitreous detachment by cleavage of proteins not at the vitreoretinal interface (as is the case with plasmin) so that potential side effects, such as the degradation of other tissues or structures of the eye, are reduced. Further, there is a need for an enzymatic method of producing a posterior vitreous detachment in which the enzyme is inhibitable readily to avoid complications resulting from removal of the enzyme or lingering enzymatic activity.

SUMMARY OF THE INVENTION

It has been discovered that an enzyme which specifically cleaves type IV collagen and fibronectin can be used to promote a partial or complete posterior vitreous detachment. By cleaving type IV collagen and fibronectin specifically, enzymatic treatment according to the invention avoids the complications of prior art intraocular enzymatic treatments for producing a posterior vitreous detachment, such as degradation of molecules comprising the vitreous or internal limiting membrane. The invention also avoids complications resulting from prior art methods involving mechanical production of posterior vitreous detachments. Thus, safer and more effective methods of producing a posterior vitreous detachment are provided by the invention.

According to one aspect of the invention, a method for treating a subject to promote a posterior vitreous detachment is provided. An enzyme which specifically cleaves type IV collagen and fibronectin is introduced into a vitreous cavity of an eye of a subject in need of such treatment, and in an amount effective to promote a posterior vitreous detachment. In some embodiments, the enzyme is introduced into the vitreous cavity by injection of an ophthalmologically acceptable carrier containing the enzyme. Preferably, the enzyme which specifically cleaves type IV collagen and fibronectin is dispase.

In certain embodiments, the concentration of dispase in the ophthalmologically acceptable carrier is between 0.1 units/milliliter and 25 units/milliliter.

In some embodiments the dispase is injected into a vitreous cavity of an eye prior to and in conjunction with an intraocular surgery to promote a posterior vitreous detachment prior to such surgery. The group of intraocular surgeries for which a posterior vitreous detachment is useful includes vitrectomy for macular hole surgery, vitrectomy for diabetic retinopathy and other proliferative vascular retinopathies, repair of a retinal detachment, prevention of a retinal detachment, subretinal surgery, submacular surgery and retinal transplantation. Preferably the concentration of dispase in the ophthalmologically acceptable carrier is between 0.1 units/milliliter and 25 units/milliliter when introduced prior to and in conjunction with an intraocular surgery as above. The amount of dispase in the ophthalmologically acceptable carrier and applied to the eye preferably is between 0.01 units and 12.5 units.

In other embodiments, administration of dispase to promote a posterior vitreous detachment can be used to treat the blinding complications of an ocular condition. Such complications are prevented or ameliorated. In these embodiments, dispase is administered to a subject having a condition such as diabetic retinopathy, central vein occlusion, proliferative vitreoretinopathy and proliferative vascular retinopathy.

It is preferred that the dispase is introduced into the vitreous cavity in an amount sufficient to promote a posterior vitreous detachment over a period of between 1 minute and 4 hours.

According to another aspect of the invention, kits for producing a posterior vitreous detachment are provided. In one embodiment, a kit includes a container containing a first amount of an enzyme which specifically cleaves type IV collagen and fibronectin and instructions for administering the enzyme to produce a posterior vitreous detachment. In another embodiment, a kit includes a first container containing a first amount of an ophthalmologically acceptable carrier including an amount of dispase effective to promote a posterior vitreous detachment, and a second container containing a second amount of ophthalmologically acceptable dispase quenching solution sufficient to quench the activity of the dispase in the eye. The concentration of dispase in the ophthalmologically acceptable carrier preferably is between 0.1 units/milliliter and 25 units/milliliter.

According to still another aspect of the invention, a device is provided. The device includes a bottle which contains an ophthalmologically acceptable carrier and an enzyme which specifically cleaves type IV collagen. The enzyme is present in an amount effective to promote a posterior vitreous detachment when administered into the vitreous cavity of an eye. In certain embodiments, the enzyme is dispase. Preferably, the concentration of dispase in the device is between 0.1 units/milliliter and 25 units/milliliter in the ophthalmologically acceptable carrier.

DETAILED DESCRIPTION OF THE INVENTION

The invention concerns a method for production of a posterior vitreous detachment (PVD) by introducing into the eye of a subject an effective amount of an enzyme which specifically cleaves type IV collagen and fibronectin at the vitreoretinal junction. The promotion of PVD by this enzymatic method allows a physician treating an intraocular condition, by surgery or other means, to avoid complications such as retinal tear or retinal detachment which frequently result as a consequence of the condition being treated or the treatment itself. The present invention also avoids the problems of prior art methods of enzymatic production of a PVD, e.g. destruction of portions of the vitreous or internal limiting membrane (ILM) by excessive or nonspecific enzyme activity. These problems are eliminated due to the discovery that the selective cleavage of type IV collagen at the vitreoretinal junction by an enzyme, preferably dispase, results in a partial or complete PVD without tissue destruction. Enzymatic induction of a posterior vitreous detachment according to the invention also has the advantage of being a controllable procedure, the control depending less on the skill of the individual practitioner than on selection of an appropriate dose of an enzyme for effective cleavage of type IV collagen and fibronectin at the vitreoretinal junction.

The invention involves the discovery that a posterior vitreous detachment can be promoted by the specific cleavage or digestion of type IV collagen molecules at the vitreoretinal junction. Detachment then advantageously can be achieved using an enzyme which, when introduced into the eye, specifically cleaves type IV collagen and fibronectin. By an "enzyme which specifically cleaves type IV collagen and fibronectin" is meant any enzyme that has a great affinity for type IV collagen and fibronectin but negligible or none for other proteins involved in structural integrity of the retina or the vitreous. Thus, enzymes useful according to the invention are those for which the activity of the enzyme in the eye is confined substantially to molecules essential for vitreoretinal attachment.

It is preferred that the enzyme which specifically cleaves type IV collagen and fibronectin is dispase. The use of dispase permits partial or complete posterior vitreous detachment without damage to the vitreous, internal limiting membrane, retina, or other eye structures. Dispase is a metalloenzyme protease produced by *Bacillus polymyxa*, and is classified as an amino-endo peptidase. Dispase is temperature and pH stable and, unlike certain other enzymes, is not quenched by inhibitors found in serum. Thus, dispase will be active in many vitreoretinal diseases where leakage of serum into the vitreous accompanies the clinical manifestations of the disease. Dispase requires the presence of divalent cations for activity; divalent cations such as $Ca^{2+}$ and $Mg^{2+}$ are abundant in the vitreous and at the vitreoretinal junction. Dispase has both fibronectinase and type IV collagenase activity. Fibronectin and type IV collagen are found at the point of attachment of the internal limiting membrane to the posterior vitreous. Dispase is thus able to cleave specifically the proteins which attach the vitreous to the internal limiting membrane and hence reduce side effects from nonspecific protein cleavage.

In contrast to other proteases used previously to produce a posterior vitreous detachment, the activity of dispase is greatly reduced by dilution of the enzyme. Thus, the activity of dispase can be reduced or terminated by introduction into the site of action of dispase in almost any ophthalmologically acceptable, physiologically compatible solution. Compositions for reducing the activity of dispase are referred to herein as "dispase quenching solutions." Preferably, the dispase quenching solution is selected from those solutions known to be ophthalmologically acceptable to one of ordinary skill in the art.

When dispase is used in conjunction with intraocular surgery, dispase activity can be terminated by introduction of an effective amount of a dispase quenching solution. The process of controlled infusion is typically part of such an intraocular surgery. Therefore, where dispase is used to promote a posterior vitreous detachment in preparation for an intraocular surgery, the intraocular surgery itself terminates the activity of the dispase and prevents excessive digestion of vitreous and retinal components. When dispase is used to prevent complications of certain ocular conditions, an effective amount of dispase quenching solution can be introduced to the vitreous cavity to terminate the enzymatic activity of dispase. As used herein with regard to dispase quenching solutions, an "effective amount" is an amount of dispase quenching solution which will reduce the dispase activity below a level at which a posterior vitreous detachment can be promoted. Of course, other equivalent methods of quenching dispase activity will be apparent to one of ordinary skill in the art, i.e. by sequestration of divalent cations and the like.

In addition to the ability to reduce dispase activity by dilution or chelation of divalent cations, dispase is preferred because it is not inhibited by the presence of serum. This property of dispase is advantageous because it permits the formation of a PVD when the subject has bleeding in the eye at the vitreoretinal junction or any leakage of serum into the vitreous which can accompany certain intraocular conditions. Certain enzymes are inhibited by the presence of serum; enzymes inhibited by serum components would be less useful for promoting a PVD in conditions where blood vessels form and break at the vitreoretinal junction, or where there is any leakage of serum into the vitreous.

One of ordinary skill in the art will be able to determine, without excessive experimentation, the enzymes which cleave type IV collagen and fibronectin and are useful for induction of a posterior vitreous detachment as described above. In preferred embodiments, the enzyme is dispase. Other proteases which cleave type IV collagen and fibronectin are also preferred. Enzymes whose activity can be quenched easily by dilution or other non-toxic means are particularly preferred.

To produce a PVD according to the invention, an enzyme which specifically cleaves type IV collagen and fibronectin is introduced into the vitreous cavity of a subject in need of a PVD. The vitreous cavity surrounds the vitreous tissue of the eye, which is a clear mass which fills the posterior cavity of the eye and forms a semi-solid support for the retina. The vitreous is firmly attached to surrounding tissues at the peripheral retina, and at the pars plana of the ciliary body, the vitreous base and around the optic disk. Adherences are also found around the retinal vessels and may be found around the macula. The vitreoretinal junction includes the internal limiting membrane; this region consists of a basement membrane and a layer of dense collagen fibrils. Between these layers exists a space across which fibrils extend. The vitreous fibrils are interwoven into the basement membrane.

It is preferred to introduce the enzyme useful in the invention, such as dispase, into the vitreous cavity by injection. The injection can be preformed according to procedures standard in the art.

The enzyme will be suspended in an opthalmologically acceptable carrier for introduction into the eye of a subject. An opthalmologically acceptable carrier is a substance which is nontoxic to the subject given the treatment and which also does not inhibit enzymatic cleavage of type IV collagen and fibronectin. An opthalmologically acceptable carrier is preferably a sterile diluent having a pH and osmolarity compatible with normal human vitreous. Examples of opthalmologically acceptable carriers include phosphate buffered saline and lactated Ringer's solution. A particularly preferred opthalmologically acceptable carrier for suspension of the enzyme is $Ca^{2+}$- and $Mg^{2+}$-free phosphate buffered saline (PBS) of pH 7.4 and 298 milliosmoles. Other opthalmologically acceptable carriers are well known in the art and can be found in standard reference texts such as Remington's Pharmaceutical Sciences (Mack Publishing Company, Easton, Pa.).

The enzyme useful for producing a PVD is introduced into the eye in amounts sufficient to produce a PVD. The amount of an enzyme, e.g. dispase, that is introduced to produce a PVD can vary according to the condition of the subject being treated, the pH of the intraocular fluid, the severity of the condition, the time available for treatment, and the like.

According to the invention, dispase can be used at a range of concentrations between 0.1 units/milliliter and 25 units/milliliter. Dispase can be obtained from commercial suppliers such as Boehringer-Mannheim (Indianapolis, Ind.), Collaborative Biomedical Products (Bedford, Mass.) and Life Technologies/GIBCO (Gaithersburg, Md.). A unit of dispase can be defined differently by different suppliers of the enzyme. For example, a unit of dispase is defined, according to the supplier Collaborative Biomedical Products, as follows. Dispase proteolytic activity is expressed in terms of units based on a caseinolytic assay. One unit is that mount of dispase which liberates from casein, in one minute, folin-positive amino acids and peptides corresponding to one micromole of tyro sine at 37° C. and pH 7.5. As defined by Life Technologies/GIBCO, a unit of dispase is equal to 181 protease units (release of folin-positive amino acids from casein equivalent to 1 mM of tyrosine per minute at pH 7.5 and 37° C.).

The total amount of dispase used in the invention can vary with, in addition to the concentration noted above, the volume introduced into the vitreous cavity of the subject's eye. The volume of dispase introduced can be a function of the size of the eye, the age of the subject, the severity of the condition and the like. Administration of the same total amount of dispase can be accomplished using a greater volume of a lower concentration dispase solution or a smaller volume of a higher concentration dispase solution, according to the needs of the subject or preferences of the practitioner. The volume of the vitreous cavity is limited, however, so that in general between 100 microliters and 500 microliters of dispase can be injected into the eye of a subject. Thus the amount of dispase which can be administered to a subject in need of such treatment is between about 0.01 and 12.5 units.

The time of treatment with dispase can be selected based on the needs of the subject to whom the dispase is administered. In some instances it can be advantageous, or even necessary, to treat a subject for a very short time. For example, a subject may manifest symptoms of an imminent retinal detachment. In such cases, a large amount of dispase can be administered for a short period of time. In other instances, for example in treatment prior to a scheduled intraocular surgery, it may be advantageous to treat a subject with a smaller amount of dispase for a longer period of time. It is contemplated that treatment times between one minute and four hours are preferred, although shorter and longer treatments are not excluded.

The use of dispase permits termination of type IV collagen and fibronectin cleavage by introduction of a dispase quenching solution. A dispase quenching solution can be selected from intraocular irrigating solutions such as physiologic saline, balanced salt solutions, lactated Ringer's solution and the like. Dispase quenching solutions can incorporate components such as ethylenediaminetetraacetic acid (EDTA) or ethylene glycol-bis(β-aminoethyl ether) N,N,N',N'-tetraacetic acid (EGTA) useful for sequestration of dispase cofactors such as $Ca^{2+}$ and $Mg^{2+}$. When dispase is used in conjunction with intraocular surgery as noted above, the controlled infusion of the eye which accompanies the surgery can quench the dispase activity. Dispase quenching solutions can be introduced to terminate dispase activity when dispase is used for the treatment of intraocular conditions with or without surgery. Dispase quenching solutions are preferably administered by injection, preferably at the site of action of dispase, i.e. the vitreoretinal junction.

The introduction into the eye of enzymes which cleave type IV collagen and fibronectin as outlined above is useful for treatment of conditions in which production of a PVD improves the prognosis of the condition, i.e. by reducing the potential for retinal detachment. As previously noted, the invention is useful in conjunction with intraocular surgery or as a non-surgical procedure.

Prior art methods for producing a PVD utilized mechanical means or relatively non-specific enzymatic reactions, both of which resulted in tissue destruction and incomplete PVDs. In contrast to the prior art methods, the use of enzymes which cleave type IV collagen, preferably dispase, provides specific cleavage of proteins of the vitreoretinal junction. Dispase is preferred in part for its specificity of cleavage at the vitreoretinal junction (i.e. type IV collagen and fibronectin) and in part because it is not quenchable by serum components.

The invention permits use of an enzyme which specifically cleaves type IV collagen and fibronectin, preferably dispase, in connection with any intraocular surgery in which production of a PVD is beneficial to a subject. As used herein, "intraocular surgery" means surgery within the eye and encompasses surgeries for many different conditions. Intraocular surgeries in which the invention can be used include vitrectomy for macular hole surgery, vitrectomy for proliferative vascular retinopathies, repair of a retinal detachment, prevention of a retinal detachment, subretinal surgery, submacular surgery and retinal transplantation. Other intraocular surgeries to which the invention is applicable will be known to those of skill in the art.

The invention can also be used for non-surgical treatment of blinding complications associated with certain conditions of the eye. Conditions treatable by the invention include those conditions in which a retinal tear or a partial or complete retinal detachment can occur if left untreated. Such conditions include diabetic retinopathy, central vein occlusion, proliferative vitreal retinopathy and proliferative vascular retinopathy. Other conditions to which the invention is applicable will be known to those of skill in the art.

As used herein, an effective amount of an enzyme which specifically cleaves type IV collagen and fibronectin to promote a PVD is a dosage large enough to produce a PVD in a subject to which the enzyme is administered. An effective amount is not, however, a dosage so large as to cause adverse side affects. Generally, an effective amount of an enzyme which specifically cleaves type IV collagen and fibronectin can vary with the subject's age and condition, as well as the extent of the condition being treated, and can be determined by one of skilled in the art. The dosage can be adjusted by the individual practitioner in the event of any complication.

The active compounds of the present invention can include an ophthamologically acceptable carrier, as defined above, which carrier is suitable for administration to a human or other animal. The term "carrier" denotes an organic or inorganic ingredient, natural or synthetic, with which the active ingredient is combined to facilitate the application. Ophthalmologically acceptable compositions can routinely contain salts, buffering agents, preservatives, compatible carriers, and optionally other therapeutic ingredients. When used in ophthalmology, the salts should be ophthalmologically acceptable, but nonophthalmologically acceptable salts can be conveniently used to prepare ophthalmologically acceptable salts thereof and are not excluded from the scope of the invention. Such opthamologically acceptable salts include, but are not limited to those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, maleic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, formic, malonic, naphthalene-2-sulfonic, benzenesulfonic and the like. Also, ophthalmologically acceptable salts can be prepared as alkaline metal or alkaline earth salts, such as sodium, potassium or calcium salts of the carboxylic acid group. The components of the ophthalmological compositions are also capable of being comingled with the molecules of the present invention, and with each other in a manner such that there is no interaction which would substantially impair the desired pharmaceutical affect.

A variety of administration routes for enzymes which cleave type IV collagen and fibronectin are available. The particular mode selected will depend of course, upon the particular subject, the severity of the condition being treated and the dosage required for therapeutic efficacy. The methods of this invention, generally speaking, can be practiced using any mode of administration that is ophthalmologically acceptable, meaning any mode that produces effective levels of the active compounds without causing clinically unacceptable adverse affects. Preferably the mode of administration is injection.

The compositions containing enzymes which cleave type IV collagen and fibronectin can be prepared by any of the methods well known in the art of pharmacy. Such methods include the step of bringing the effective ingredient into association with a carrier which constitutes one or more accessory ingredients. In general, the compositions are prepared by uniformly and intimately bringing the enzyme which specifically cleaves type IV collagen and fibronectin into association with a liquid carrier, a finally divided solid carrier, or both. Injectable compositions are contemplated and suitable formulations can be found in Remington's Pharmaceutical Sciences (Mack Publishing Company, Easton, Pa.).

Preferred compositions suitable for intraocular administration conveniently comprise a sterile aqueous preparation of the enzyme which specifically cleaves type IV collagen and fibronectin, preferably dispase. This aqueous preparation can be formulated according to known methods using suitable dispersing or wetting agents and dispensing agents. The sterile injectable preparation can also be a sterile injectable solution or suspension in a non-toxic ophthalmologically acceptable diluent or solvent. It is important that any solution applied to an intraocular cavity be free of any factors that would injure intraocular tissue. Thus it preferably is sterile, approximately iso-osmotic, and at the correct pH compatible with enzyme activity and intraocular tissues. As noted above, a particularly preferred solution for preparation of an injectable suspension of the enzyme is $Ca^{2+}$- and $Mg^{2+}$-free phosphate buffered saline (PBS) of pH 7.4 and 298 milliosmoles. Other solutions useful in preparation of injectable suspensions of enzymes useful in the invention are known to those of ordinary skill in the art.

According to another aspect of the invention, kits for producing a posterior vitreous detachment are provided. Certain kits include a container containing an amount of an enzyme which specifically cleaves type IV collagen and fibronectin in an ophthalmologically acceptable carrier effective to produce a posterior vitreous detachment and instructions for administering such an enzyme for producing a posterior vitreous detachment. Other kits contain, in individual containers, an ophthalmologically acceptable carrier including an amount of dispase effective to promote a posterior vitreous detachment and an ophthalmologically acceptable dispase quenching solution sufficient to quench the activity of the dispase. In one embodiment of the invention, the kit contains dispase in the ophthalmologically acceptable carrier in a concentration of between 0.1 units/milliliter and 25 units/milliliter. All such kits can have instructions for the use of the enzymes and/or quenching solutions according to the invention.

The kits are enclosed in a package, such as a box, blister pack or similar packing vehicle used conventionally to hold containers of liquid. The package can be coated with an impervious cover to assist in protecting the sterility of the contents during transport and storage. The containers preferably are glass bottles, but can be formed of any inert material such as a rigid or flexible plastic in the form of bottles or bags that allow transport and storage of liquid without loss of fluid or contamination of the contents.

According to another aspect of the invention, a device is provided. The device comprises a bottle containing an enzyme which specifically cleaves type IV collagen and fibronectin in an ophthalmologically acceptable carrier. The enzyme is present in the bottle in an amount effective to promote a posterior vitreous detachment when administered by an individual practitioner to a vitreous cavity of an eye. Preferably the enzyme contained in the bottle is dispase. The bottle can be formed of any material which does not inhibit the activity of the enzyme contained therein. For example, the bottle can be made of glass or plastic. The bottle can have a piercable septum through which the active composition can be removed. In use, the septum of the bottle is pierced by the needle of a syringe, the enzyme in ophthalmologically acceptable carrier solution is removed by syringe from the bottle and injected into the eye. The bottle preferably contains dispase at a concentration between about 0.1 units/milliliter and 25 units/milliliter (U/ml).

EXAMPLES

Example 1

Preparation of Dispase

Dispase was obtained as a powder from Life Technologies (Gibco/BRL, Gaithersburg, Md.). The powder was reconstituted in phosphate buffered saline (pH 7.4) at concentrations from 0.1 to 25.0 u/ml. The reconstituted dispase was filtered through a 0.2 micron filter (Millipore, Bedford, Mass.), divided into 5.0 ml aliquots and stored at $-20°$ C. until use. Prior to use, the dispase was filtered again through a 0.2 micron filter and aspirated into a 1 ml tuberculin syringe with a 25 gauge, ¾ inch needle for injection via the pars plana of the eye.

Example 2

Efficacy of Dispase in Inducing a Posterior Vitreous Detachment at 2 U/ml

Ten domestic pig eyes were obtained from a local slaughterhouse within 3 hours of death. 0.5 ml of dispase solution, at a concentration of 2 U/ml was injected in the mid-vitreal cavity of the eyes. The same amount of calcium-magnesium free phosphate-buffered saline (PBS) was injected into another set of 10 eyes as controls. Eyes were incubated for 120 minutes at $37°$ C. in a humidified atmosphere of 5% $CO_2$ and 95% air. At the end of this period a circumferential incision was made at 2 mm posterior to ora serrata and the anterior segment was removed and posterior vitreous detachment was graded as complete, incomplete or none. None of the control eyes revealed posterior vitreous detachment, whereas in 7/10 (70%) of the dispase-treated eyes a complete posterior vitreous detachment developed. The remaining 3/10 (30%) dispase-treated eyes had an incomplete posterior vitreous detachment. The rate of posterior vitreous detachment occurrence with dispase treatment was statistically higher than the controls ($\kappa^2=5.128$, $p=0.0154$).

Example 3

Time Course of Dispase Treatment 0.5 ml of 2U/ml dispase solution was injected into the mid-vitreal cavity of 35 enucleated pig eyes. Eyes were incubated at $37°$ C. in a humidified atmosphere of 5% $CO_2$ and 95% air for 5, 15, 30, 45, 60, 90 and 120 minutes. At each time points 5 eyes were selected randomly, dissected and posterior vitreous detachment was graded. At 5 and 15 minutes posterior detachment was not observed in any of the eyes; at 30 minutes 2 (40%) eyes developed an incomplete posterior vitreous detachment, whereas in the remaining 3 (60%) eyes posterior vitreous detachment was not observed; at 45 minutes 2 (40%) eyes revealed a complete posterior vitreous detachment, 1 (20%) eye an incomplete posterior vitreous detachment and the remaining 2 (40%) eyes no posterior vitreous detachment; at 60 minutes the rate of complete posterior vitreous detachment increased to 60% (3 eyes) whereas 1 (20%) eye developed an incomplete posterior vitreous detachment and the remaining 1 (20%) eye did not develop posterior vitreous detachment; at 90 and 120 minutes 4 (80%) of the eyes revealed a complete posterior vitreous detachment and 1 (20%) eye had an incomplete posterior vitreous detachment.

In a separate experiment, the time course of low-dose dispase treatment was studied. For this experiment, 0.5 ml of dispase at a concentration of 0.1 U/ml was injected into the mid-vitreal cavity of 35 enucleated pig eyes. Eyes were incubated at 37 ° C. in a humidified atmosphere of 5% $CO_2$ and 95% air for 5, 15, 30, 45, 60, 90 and 120 minutes. At each time point, posterior vitreous detachment was graded in 5 eyes. At 5 and 15 minutes a complete posterior vitreous detachment was observed in 1 (20%), incomplete posterior vitreous detachment in 2 (40%) and no posterior vitreous detachment in 2 (40%) eyes. At 30 and 45 minutes the rate of complete posterior vitreous detachment increased to 60% (3 eyes); incomplete posterior vitreous detachment developed in 1 (20%) eye and no posterior vitreous detachment was observed in 1 (20%) eye. Incubations for and above 60 minutes resulted in either complete or incomplete posterior vitreous detachment in all eyes (3 (60%) eyes complete, 2 (40%) eyes incomplete at 60 minutes; 4 (80%) eyes complete, 1 (20%) eye incomplete at 90 minutes; 5 (100%) eyes complete at 120 minutes).

Example 4

Dose Effect of Dispase 0.5 ml of dispase solutions at concentrations of 0.05, 0.1, 0.25, 0.5, 1.0, 2.0, 3.0, and 4.0 U/ml were injected in the mid-vitreal cavity of adult domestic pig eyes. Eyes were incubated for 120 minutes and then the induction of posterior vitreous detachment was determined. At 0.05 U/ml complete posterior vitreous detachment was observed in 3/10 (30%) eyes, incomplete posterior vitreous detachment in 1/10 (10%) eye and no posterior vitreous detachment in the remaining 6/10 (60%) eyes. With 0.1 U/ml complete posterior vitreous detachment rate increased to 80% (12/15 eyes) and incomplete posterior vitreous detachment rate to 13.3% (2/15 eyes). Only 1/15 (6.7%) eye had no posterior vitreous detachment. Doses above 0.1 U/ml revealed comparable efficacy (80% complete, 20% incomplete posterior vitreous detachment with 0.25 U/ml; 90% complete, 10% no posterior vitreous detachment with 0.5 and 1.0 U/ml; 75% complete, 15% incomplete, 5% no posterior vitreous detachment with 2.0 U/ml; 80% complete, 20% incomplete with 3.0 U/ml; 80% complete, 10% incomplete, 10% no posterior vitreous detachment with 4.0 U/ml).

Example 5

Time Course of High Concentration of Dispase Treatment 0.5 ml of dispase solution at a concentration of 4.0 U/ml was injected int the mid-vitreal cavity of 15 enucleated pig eyes. Eye cups were incubated for 15, 30 and 45 minutes and the induction of posterior vitreous detachment was determined. At 15 minutes 2/5 (40%) eyes had developed a complete posterior vitreous detachment, 1/5 (10%) eye had developed an incomplete posterior vitreous detachment and the remaining 2/5 (40%) eyes revealed no posterior vitreous detachment. At 30 minutes the rate of posterior vitreous detachment induction was comparable: 1/5 (20%) eye with complete posterior vitreous detachment, 2/5 (40%) eyes with incomplete posterior vitreous detachment and 1/5 (20%) eyes with no posterior vitreous detachment). At 45 minutes the rate of complete posterior vitreous detachment increased to 60% (3/5 eyes) whereas 1/5 (20%) of the remaining eyes had an incomplete posterior vitreous detachment and the other revealed no posterior vitreous detachment. Overall at 45 minutes 80% of the eyes (4/5) developed either a complete or incomplete posterior vitreous detachment.

Example 6

Dose Effect of Dispase Treatment at 15 minutes Treatment Time 0.5 ml of dispase solutions at concentrations of 1.0, 2.0, 5.0, 10.0 and 25.0 U/ml were injected in the mid-vitreal cavity often enucleated pig eyes from each group. The same amount of calcium-magnesium free phosphate-buffered saline was injected into another set of 10 eyes as controls. Eyes were incubated at 37 ° C. in a humidified atmosphere of 5% $CO_2$ and 95% air for 15 minutes and at the end of this period they were opened and posterior vitreous detachment was graded. In control eyes 1/10 (10%) had a complete, and 2/10 (20%) had an incomplete posterior vitreous detachment; 7/10 (70%) had no posterior vitreous detachment developed. At concentrations of 1 and 2 U/ml a complete posterior vitreous detachment was observed in 4/10 (40%) eyes, an incomplete posterior vitreous detachment in 3/10 (30%) and no posterior vitreous detachment in 3 (30%) eyes. At 5 U/ml, the rate of complete posterior vitreous detachment increased to 60% (6/10 eyes) and incomplete posterior vitreous detachment was observed in 20% (2/10 eyes). Only 2/10 (20%) eyes had no posterior vitreous detachment. Injection of dispase at a concentration of 10 U/ml yielded a complete posterior vitreous detachment in 8/10 (80%) eyes, incomplete posterior vitreous detachment in 1/10 (10%) eye and no posterior vitreous detachment in 1/10 (10%) eye. At 25 U/ml the rate of complete posterior vitreous detachment was 50% (5/10 eyes) and incomplete posterior vitreous detachment was 40% (4/10 eyes), whereas in 1/10 (10%) eye a posterior vitreous detachment did not develop. The lowest dose that induced a statistically higher rate of posterior vitreous detachment than the control was found to be 5 U/ml ($p=0.027$ for complete posterior vitreous detachment).

Example 7

Ultrastructural Analysis of Vitreoretinal Interface in Dispase Treated Eyes 0.5 ml of dispase solutions at concentrations of 0.1 U/ml (287 mOsm, pH=7.4, total dose=0.05 U) and 5 U/ml (301 mOsm, pH=7.4, total dose =2.5 U) were injected into the vitreous of 3 enucleated adult domestic pig eyes, and eyes were incubated at 37° C. in a humidified atmosphere of 5% $CO_2$ and 95% air for 120 and 15 minutes, respectively. Intravitreal injections of the same amount of calcium-magnesium free PBS were used as a control in an additional 3 eyes. After incubation, the globe was punctured at 4 points, 3 mm from the limbus; fixed in an isotonic fixative solution composed of 1% formaldehyde and 1.25% glutaraldehyde in phosphate-buffered saline at 4° C. for 24 hours. The anterior segment was then removed, the retina was dissected, post-fixed in 1% osmium tetroxide in 0.16 M cacodylate buffer (pH 7.4) for 1 hour, stained in 1% uranyl acetate in 0.1 M sodium acetate buffer, dehydrated in a graded series of ethyl alcohol baths (30–100%), and embedded in Epon 812. The plastic embedded specimens were sectioned to 1 micrometer thickness, stained for 1 minute with Richardson's stain, and rinsed in distilled water. Ultrathin sections were cut with an ultramicrotome (Ultramicrotome MT-2, Sorvall, Conn.) and examined in a transmission electron microscope (Model 100B, JEOL Ltd., Tokyo, Japan) using an acceleration voltage of 80 kV.

The retina was fixed and dehydrated for scanning electron microscopy as described above. Samples were then embedded in Epon 812 without catalyst and placed in gelatin capsules. They were frozen at −80° C. for 20 minutes and then cracked into halves. The resin was removed by propylene oxide, and the specimens were desiccated for 5 minutes in hexamethylsilazane, followed by air drying overnight. They were then glued to metal stubs with silver paste and coated with 30 nanometer gold palladium. Samples were examined in a Hitachi S-450 scanning electron microscope (Tokyo, Japan) at 15°–90° tilting angles using an acceleration voltage of 15 kV.

On light microscopy, the retinal architecture was not affected by dispase treatment either at 0.1 U/ml for 120 minutes or 5 U/ml for 15 minutes. The wall of the blood vessels was intact. On transmission electron microscopy control eyes showed presence of collagen fibrils in the posterior hyaloid often oriented parallel to the surface and adjacent to the lamina rara externa of the internal limiting membrane. In dispase treated eyes collagen fibrils of the posterior hyaloid disappeared along with the lamina rara externa of the internal limiting membrane. The lamina densa lost its distinct borders and became an amorphous granular structure. In scanning electron microscopy of the control eyes the internal limiting membrane appeared as a homogeneous undulating membrane that obscured the underlying retinal surface structure. Its thickness showed regional variations and was the thickest at the posterior pole. Müller cell end plates could be seen to terminate as fan-shaped structures. After treating with dispase at both concentrations the internal limiting membrane disappeared, exposing a mosaic pattern of the pig's retinal surface. This mosaic pattern appeared to be the impression of the Müller cell's end-foot plate.

Example 8

Cytotoxicity Assays of Dispase Treated Retina 0.5 ml of 0.1 U/ml (287 mOsm, pH=7.4, total dose=0.05 U) and 5 U/ml (301 mOsm, pH=7.4, total dose=2.5 U) dispase solutions were injected into the mid-vitreal cavity of 5 adult domestic pig eyes. The eyes were incubated at 37° C. in a humidified atmosphere of 5% $CO_2$ and 95% air for 120 and 15 minutes, respectively. Fellow eyes that had received the same amount of intravitreal calcium-magnesium free phosphate-buffered saline were used as controls. At the end of the incubation period, the eyes were hemisected; the retina was dissected and transferred to a petri dish containing modified Eagle's medium. Pieces of retina 5×5 mm in size were cut under a dissecting microscope and transferred onto a glass slide. Cell viability was assessed by Live/Dead Viability/Cytotoxicity Kit® (Molecular Probes, Eugene, Oreg.) which is known to be more sensitive than conventional colorimetric methods. This kit contains two probes: calcein and ethidium homodimer. It relies on intracellular esterase activity to identify the living cells, which cleaves the calcein to form a green fluorescent membrane-impermeable product. Ethidium can easily pass through the compromised membranes in dead cells and attach to the DNA, yielding a red fluorescence. At least three different areas each containing approximately 250 cells was counted under 100× magnification. The retina cell viability was expressed as the average ratio of live cells to the total number of cells in these three different areas.

Cell viability was also checked in 20 human cadaver eyes that were either incubated for 15 minutes (n=15) after being injected in the mid-vitreal cavity with 0.5 ml of dispase at a concentration of 5 U/ml (301 mOsm, pH=7.4, total dose=2.5 U) or 120 minutes after being injected with 0.5 ml of Dispase at a concentration of 0.1 U/ml (287 mOsm, pH=7.4, total dose=0.05 U). Fellow eyes that had received the same amount of intravitreal calcium and magnesium-free PBS were used as controls.

After injection and incubation for appropriate times with Dispase solutions whole retinal cell viability did not change significantly in both pig (94.4±3.5% vs. 92.7±2.5% at 0.1 U/ml, p=0.63; 96.2±2.3% vs. 97.3±1.5% at 5 U/ml, p=0.74) and human cadaver eyes (93.8±5.0% vs. 3.7% at 0.1 U/ml, p=0.53; 92.8±2.0% vs. 95.5±2.0% at 5.0 U/ml, p=0.95).

Example 9

Production of a Posterior Vitreous Detachment in Human Eyes Using Dispase

The efficiency of Dispase to induce a posterior vitreous detachment was also tested in 20 human cadaver eyes. Eyes from young donors with a low chance of spontaneous posterior vitreous detachment were included in this study. Death-to-experiment time was restricted to <72 hours, although the effect of death on the strong adhesion between the retina and the vitreous is insignificant. Upon receipt the suprachoroidal space of the posterior poles of the human eyes were sealed by adhering the iris root to the sclera using a cyanoacrylate glue. 0.5 ml of dispase at a concentration of 5 U/ml (total dose=2.5 U) was injected into the mid-vitreal cavity. Fellow eyes received the same amount of calcium-magnesium-free PBS injections and were used as control assuming that the vitreal changes would be comparable. Eyes were incubated for 15 minutes at 37° C. in a humidified atmosphere of 5% $CO_2$ and 95% air, hemisected and the presence of posterior vitreous detachment was graded.

Death-to-experiment time was 23.2±12.6 hours (7.1–54.1) for the human cadaver eyes. The average age of the donors was 39.1±13.2 (18–61). Two of the eyes were from female donors, and 18 of them were from male donors. Eight (40%) of them had died due to a traffic accident, 5 (25%) from myocardial infarction, 3 (15%) from cerebrovascular accident, 3 (15%) from respiratory failure, and 1 (5%) from cancer. None of the eyes had signs of ocular trauma. Nineteen (95%) of the eyes that had been injected with dispase revealed a complete posterior vitreous detachment, whereas one eye (5%) had an incomplete posterior vitreous detachment. None of the eyes that had received PBS injections had a complete posterior vitreous detachment, however one of them (5%) had an incomplete posterior vitreous detachment.

Example 10

Mechanical Properties of Dispase Treated Porcine Retinas

The structural integrity of the treated retina was estimated by measuring the elastic constant (k) and maximal retinal stretching before fracture. For this purpose, 0.5 ml of dispase at a concentration of 0.1 U/ml (287 mOsm, pH=7.4, total dose=0.05 U) and 5 U/ml (301 mOsm, pH=7.4, total dose=2.5 U) was injected into the mid-vitreal cavity of 5 human cadaver eyes. The same amount of intravitreal calcium-magnesium free PBS injections were used as controls. The eyes were incubated at 37° C. in a humidified atmosphere of 5% $CO_2$ and 95% air for 120 and 15 minutes, respectively. The anterior segment was then removed, the sensory retina was dissected out and transferred into a petri dish containing $CO_2$-free medium (Gibco, Grand Island, N.Y.). Under the dissecting microscope, strips of retina were cut which were 5×20 millimeter in size and extending from the periphery towards the posterior pole. Care was taken to avoid relatively vesselrich regions and the thicker peripapillary retina in order to minimize the variation in measurements. Strips with visible tears were discarded. A teflon plate was then moved under the free-floating strips and elevated to allow the retinal strip to spread on the surface of the teflon plate. Excess moisture around the tissue was removed with a filter paper and two thin (20 millimeter in length and 0.5 millimeter in diameter) plastic threads were glued to the corners at both ends of the retinal strip. The strip was elevated and clipped on two metal arms. A ruler was attached on the side of the metal arms. Small pre-prepared plastic bags of 25, 50, 100, 200, 400 and 600 mg phosphate-buffered saline were attached to the metal arms to allow the plastic threads to stretch the retinal strips. At each instance the length of the stretched retinal strip was read from the ruler and recorded. Once the retinal strip exceeded its elastic limits it fractured, and the ratio of the longest distance the strip stretched before fracture to the original length was recorded as the maximal retinal stretch before fracture. The elastic constant (k) was defined as the ratio of the applied force (F) to the amount of retinal stretch (ΔL)(k=|weight of the plastic bag× gravitational constant|/[Final length of the retinal strip-Initial length of the retinal strip|). The amount of retinal stretch was plotted as a function of the force applied (stress-strain plot), and the slope of the linear regression line was calculated as the elastic constant of the retina using a computer with Sigmaplot 2.0 software (Jandel Corp., USA). The average of three measurements from a single eye was accepted as the elastic constant for that retina.

The two described regimens of Dispase treatment did not alter the elastic properties of the sensory retina. The elastic constant of the sensory retina incubated either with 5 U/ml Dispase for 15 minutes (2.3±1.0 vs. 2.0±0.7 N.m$^{-1}$, p=0.46), or with 0.1 U/ml Dispase for 120 (2.3±0.8 vs. 2.3±1.3 N.m$^{31}$ 1, p=0.47) were similar to the control. Likewise, maximal retinal stretching before fracture was comparable to the control (2.5±0.3% vs. 2.2±0.4% for the treatment with 5 U/ml for 15 minutes, p=0.71, and 2.4±0.6% vs. 2.3±0.5% for the treatment with 0.1 U/ml for 120 minutes, p=0.38).

All patents and other documents disclosed in this application are incorporated in their entirety herein by reference.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. A method for treating a subject to promote a posterior vitreous detachment comprising introducing into a vitreous cavity of an eye of a subject in need of such treatment an enzyme which specifically cleaves type IV collagen and fibronectin in an amount effective to promote a posterior vitreous detachment.

2. The method of claim 1 wherein the enzyme is introduced into the vitreous cavity by injection of an ophthalmologically acceptable carrier containing the enzyme into the vitreous cavity.

3. The method of claim 1 wherein the enzyme is dispase.

4. The method of claim 3 wherein the dispase is introduced into the vitreous cavity by injection of an ophthalmologically acceptable carrier containing dispase into the vitreous cavity.

5. The method of claim 4 wherein the concentration of dispase in the carrier is between 0.1 units/milliliter and 25 units/milliliter.

6. The method of any one of claims 3, 4 or 5 wherein the dispase is introduced prior to and in conjunction with an intraocular surgery to promote a posterior vitreous detachment prior to the intraocular surgery.

7. The method of claim 6 wherein the intraocular surgery is selected from the group consisting of vitrectomy for macular hole surgery, vitrectomy for proliferative vascular retinopathies, repair of a retinal detachment, prevention of a retinal detachment, subretinal surgery, submacular surgery, retinal transplantation, and vitrectomy for ocular trauma.

8. The method of claim 6 wherein the dispase is in an ophthalmologically acceptable carrier and the concentration of dispase in the carrier is between 0.1 units/milliliter and 25 units/milliliter.

9. The method of claim 6 wherein the dispase is in an ophthalmologically acceptable carrier and the amount of dispase is between 0.01 units and 12.5 units.

10. The method of claim 3 wherein dispase is administered to a subject having a condition selected from the group consisting of diabetic retinopathy, central vein occlusion, proliferative vitreoretinopathy and proliferative vascular retinopathy.

11. The method of claim 3 wherein the dispase is introduced into the vitreous cavity in an amount sufficient to promote a posterior vitreous detachment between 1 minute and 4 hours.

12. A kit for producing a posterior vitreous detachment comprising a package including a) a container containing an amount of an ophthalmologically acceptable carrier including an amount of an enzyme which specifically cleaves type IV collagen and fibronectin effective to promote a posterior vitreous detachment; and, b) instructions for administering the enzyme to produce a posterior vitreous detachment.

13. A kit for producing a posterior vitreous detachment comprising a package including a) a first container containing a first amount of an ophthalmologically acceptable carrier including an amount of dispase, having an activity, effective to promote a posterior vitreous detachment; and, b) a second container containing a second amount of an ophthalmologically acceptable quenching solution sufficient to quench the activity of the dispase.

14. The kit of claim 13 wherein the concentration of dispase in the ophthalmologically acceptable carrier is between 0.1 units/milliliter and 25 units/milliliter.

15. A device comprising a bottle containing an ophthalmologically acceptable carrier and an enzyme which specifically cleaves type IV collagen and fibronectin in an amount effective to promote a posterior vitreous detachment when administered to a vitreous cavity of an eye.

16. The device of claim 15 wherein the enzyme is dispase.

17. The device of claim 16 wherein the concentration of dispase is between 0.1 units/milliliter and 25 units/milliliter.

* * * * *